(12) United States Patent
Iscovich

(10) Patent No.: US 9,861,678 B2
(45) Date of Patent: *Jan. 9, 2018

(54) CASEIN PEPTIDE FOR USE IN THE TREATMENT OF UTERINE INFECTIONS

(71) Applicant: Mileutis Ltd., Gan Yavne (IL)

(72) Inventor: Jose Mario Iscovich, Gan Yavne (IL)

(73) Assignee: Mileutis Ltd., Gan Yavne (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/946,186

(22) Filed: Nov. 19, 2015

(65) Prior Publication Data

US 2016/0324915 A1 Nov. 10, 2016

Related U.S. Application Data

(63) Continuation of application No. 13/641,959, filed as application No. PCT/IL2011/000325 on Apr. 17, 2011, now Pat. No. 9,220,751.

(60) Provisional application No. 61/326,390, filed on Apr. 21, 2010.

(51) Int. Cl.
| | |
|---|---|
| *A01N 37/18* | (2006.01) |
| *A61K 38/00* | (2006.01) |
| *A61P 31/04* | (2006.01) |
| *A61K 38/01* | (2006.01) |
| *A61K 38/17* | (2006.01) |
| *A61K 9/00* | (2006.01) |
| *A61K 35/20* | (2006.01) |

(52) U.S. Cl.
CPC .......... *A61K 38/018* (2013.01); *A61K 9/0019* (2013.01); *A61K 9/0034* (2013.01); *A61K 38/1709* (2013.01); *A61K 35/20* (2013.01)

(58) Field of Classification Search
CPC .. A61K 35/20; A61K 38/018; A61K 38/1709; A61K 9/0019; A61K 9/0034
See application file for complete search history.

(56) References Cited

U.S. PATENT DOCUMENTS

| | | | |
|---|---|---|---|
| 3,764,670 A | 10/1973 | Katzirkatchalsky et al. | |
| 3,930,058 A | 12/1975 | Kumar et al. | |
| 5,223,253 A * | 6/1993 | Hall | A61K 39/002 424/269.1 |
| 5,330,975 A | 7/1994 | Isoda et al. | |
| 5,506,209 A | 4/1996 | Mukerji et al. | |
| 5,538,952 A | 7/1996 | Mukerji et al. | |
| 5,622,927 A | 4/1997 | Hangay et al. | |
| 5,707,968 A | 1/1998 | Mukerji et al. | |
| 5,785,990 A | 7/1998 | Langrehr | |
| 5,952,009 A * | 9/1999 | Neurath | A61K 38/1709 424/535 |
| 5,968,901 A | 10/1999 | Andersson et al. | |
| 7,915,008 B2 * | 3/2011 | Larsen | C07K 14/473 435/4 |
| 7,968,513 B2 | 6/2011 | Iscovich et al. | |
| 8,338,363 B2 | 12/2012 | Iscovich et al. | |
| 9,220,751 B2 * | 12/2015 | Iscovich | A61K 38/1709 |
| 2004/0167073 A1 | 8/2004 | Sidelman | |
| 2007/0203060 A1 | 8/2007 | Sidelman | |
| 2009/0069218 A1 | 3/2009 | Iscovich et al. | |
| 2009/0305947 A1 | 12/2009 | Iscovich et al. | |

FOREIGN PATENT DOCUMENTS

| | | | |
|---|---|---|---|
| CZ | 20030008 A3 | 7/2004 | |
| WO | 0005839 | 2/2000 | |
| WO | 02/05839 A1 | 1/2002 | |
| WO | WO2006/117784 | * 11/2006 | .............. A61K 38/17 |
| WO | WO2007/116410 | * 10/2007 | .............. A61K 38/17 |
| WO | 2009033784 | 3/2009 | |

OTHER PUBLICATIONS

Tidona, Flavio et al., "Bioactive peptides in dairy products". Italian Journal of Animal Science [Online], 8.3 (2009): 315-340.
Sheldon, I.M et al., "Effect of intrauterine administration of oestradiol on postpartum uterine bacterial infection in cattle". Animal Reproduction Science, vol. 81, Issue 1, (2004): 13-23.
Santos TMA et al., "Diversity and Succession of Bacterial Communities in the Uterine Fluid of Postpartum Metritic, Endometritic and Healthy Dairy Cows". PLoS One 7(12), (2012): e53048.
Rizzello, C.G. et al., "1.Antibacterial Activities of Peptides from the Water-Soluble Extracts of Italian Cheese Varieties". Journal of Dairy Science, vol. 88, Issue 7, (2005): 2348-2360.
Rana M, et al., "Antimicrobial peptides: a new dawn for regulating fertility and reproductive tract infections". J Endocrinol Reprod 10(2), (2006): 88-95.
Minervini, F. et al. "Angiotensin I-Converting-Enzyme-Inhibitory and Antibacterial Peptides from Lactobacillus Helveticus PR4 Proteinase-Hydrolyzed Caseins of Milk from Six Species". Applied and Environmental Microbiology 69.9 (2003): 5297-5305.
Bondurant, R.H., "Inflammation in the bovine female reproductive tract". J. Anim. Sci., 77 (1999):101-110.
Farrell, Jr. et al., "Nomenclature of the Proteins of Cows' Milk—Sixth Revision," Journal of Dairy SCience, vol. 87, pp. 1641-1674, 2004.
Merrifield, "Solid Phase Peptide Synthesis. I. The Synthesis of a Tetrapeptide," Journal of the American Chemical Society, vol. 85 (14), pp. 2149-2154, 1963.

(Continued)

*Primary Examiner* — Marcela M Cordero Garcia
(74) *Attorney, Agent, or Firm* — Wiggin and Dana LLP; Gregory Rosenblatt; Andrew Bochner

(57) ABSTRACT

The present disclosure relates to a casein peptide for use in the treatment of an uterine infection in a female mammalian animal, to methods of treatment of such infections by administering to a female mammalian animal at least one casein peptide, to the use of casein peptide for the preparation of a pharmaceutical composition for treatment of uterine infection and to a kit for said treatment. The casein peptide is preferably a casein hydrolysate, e.g. obtained by trypsin hydrolysis of casein protein. The female mammalian animal is, in accordance with some embodiments, a lactating animal, the infection being a post-partum infection.

21 Claims, No Drawings

(56) References Cited

OTHER PUBLICATIONS

Shamay, et al., "Infusions of Casein Hydrolyzates into the Mammary Gland Disrupt Tight Junction Integrity and Induce Involution in Cows," Journal of Dairy Science, vol. 86, pp. 1250-1258, 2003.
PCT/IL2011/000325, International Search Report, dated Aug. 3, 2011.
Elad, Daniel et al., "Bovine Necrotic Vulvovaginitis Associated with Porphyromonas levii," Emerging Infectious Diseases, vol. 10, No. 3, pp. 505-407, Mar. 2004.
Jenness, R. et al., "Casein and Lactose Concentrations in Milk in 31 Species are Negatively Correlated," Esperienta 43, BirkHauser Verlag, CH-4010 Basel, Switzerland, pp. 1015-1018, Feb. 1987.
Lewis, Gregory S., "Uterine Health and Disorders," Symposium: Health Problems of the Postpartum Cow, J. Dairy Sci. vol. 80, No. 5, pp. 984-994, May 1997.
Thinkhamrop, J. et al., "Prophylactic Antibiotics for Transcervical Intrauterine Procedures," The Cochrane Collaboration, Published by John Wiley & Sons, Ltd., Issue 3, pp. 1-12, Nov. 2006.

* cited by examiner

SEQUENCE LISTING

```
<160> NUMBER OF SEQ ID NOS: 6

<210> SEQ ID NO 1
<211> LENGTH: 5
<212> TYPE: PRT
<213> ORGANISM: Bovine

<400> SEQUENCE: 1

Ser Ser Ser Glu Glu
1               5

<210> SEQ ID NO 2
<211> LENGTH: 25
<212> TYPE: PRT
<213> ORGANISM: BOVINE

<400> SEQUENCE: 2

Arg Glu Leu Glu Glu Leu Asn Val Pro Gly Glu Ile Val Glu Ser Leu
1               5                   10                  15

Ser Ser Ser Glu Glu Ser Ile Thr Arg
            20                  25

<210> SEQ ID NO 3
<211> LENGTH: 21
<212> TYPE: PRT
<213> ORGANISM: BOVINE

<400> SEQUENCE: 3
```

```
Gln Met Glu Ala Glu Ser Ile Ser Ser Ser Glu Glu Ile Val Pro Asp
1               5                   10                  15

Ser Val Glu Gln Lys
            20

<210> SEQ ID NO 4
<211> LENGTH: 21
<212> TYPE: PRT
<213> ORGANISM: BOVINE

<400> SEQUENCE: 4

Lys Asn Thr Met Glu His Val Ser Ser Ser Glu Glu Ser Ile Ile Ser
1               5                   10                  15

Asn Glu Thr Tyr Lys
            20

<210> SEQ ID NO 5
<211> LENGTH: 17
<212> TYPE: PRT
<213> ORGANISM: BOVINE

<400> SEQUENCE: 5

Lys Val Asn Glu Leu Ser Lys Asn Ile Gly Ser Glu Ser Thr Glu Asp
1               5                   10                  15

Gln

<210> SEQ ID NO 6
<211> LENGTH: 20
<212> TYPE: PRT
<213> ORGANISM: BOVINE

<400> SEQUENCE: 6

Pro Thr Leu Asn Arg Glu Gln Leu Ser Thr Ser Glu Glu Asn Ser Lys
1               5                   10                  15

Lys Thr Val Asp
            20
```

CASEIN PEPTIDE FOR USE IN THE
TREATMENT OF UTERINE INFECTIONS

CROSS-REFERENCE TO RELATED
APPLICATION

This application is a continuation of U.S. patent application Ser. No. 13/641,959 that was filed on Dec. 24, 2012 that is a United States National Stage application under 35 USC §371 of, and claims priority to, International Application Number PCT/IL2011/000325, filed Apr. 17, 2011 that claims priority to U.S. Provisional Application Ser. No. 61/329,390 that was filed on Apr. 21, 2010. The disclosures of both U.S. Ser. No. 13/641,959 and U.S. 61/329,390 are fully incorporated herein by reference in their entireties.

FIELD OF THE INVENTION

The present invention relates to casein peptides and to therapeutic uses thereof.

BACKGROUND OF THE INVENTION

The casein protein comprises three fractions, $\alpha$, $\beta$ and $\gamma$, according to their electrophoretic mobility. Casein hydrolysate is the hydrolyzed form of casein which includes, among others, the active beta-casein-derived peptide. It has been established that casein hydrolysate plays a role in immune responses against microbial and viral infections.

For example, U.S. Pat. No. 3,764,670 describes the antibacterial activity of casein fragments (obtained by proteolytic activity) and discloses proteolytic casein digests possessing antimicrobial properties against microorganisms.

U.S. Pat. Nos. 5,506,209, 5,538,952 and 5,707,968, all to Mukerji et al., and U.S. Pat. No. 5,968,901 to Andersson, et al., describe the administration of only human beta-casein, recombinant human beta-casein, and hydrolysates of both, in a liquid enteral formula, for treating respiratory syncytial virus, otitis media, H. influenza and other infections in infants.

U.S. Pat. No. 5,330,975 describes the use of sialic-acid binding kappa-casein and kappa-casein peptides for the neutralization of bacterial endotoxins, such as cholera toxin.

U.S. Patent Application publication No. 2009/0305947 describe the use of casein peptides and in particular casein hydrolysate for the management of the reproductive cycle of livestock and farm animals. U.S. Patent Application publication No. 2009/0069218 describe the use of casein peptides and in particular casein hydrolysate as a method for decreasing the length of the dry period of a lactating livestock animal, for increasing its milk yield and milk hygiene after parturition and for improving the livestock welfare.

SUMMARY OF THE INVENTION

In accordance with a first of its aspects, the present disclosure provides a casein peptide for use in the treatment of a uterine infection in a female mammalian animal. Such treatment facilitates, inter alia, good postpartum management in mammalian animals The present disclosure also provides, in accordance with a second of its aspects, a method for treatment of a uterine infection, the method comprises administrating to a female mammalian animal in need of treatment of uterine infection, an amount of at least one casein peptide, the amount being effective to treat an uterine infection in the mammalian animal.

The present disclosure also provides, in accordance with a third of its aspects, the use of at least one casein peptide, for the preparation of a pharmaceutical composition for the treatment of a uterine infection in a female mammalian animal in need of treatment of uterine infection.

In addition, the present disclosure also provides, in accordance with an addition aspect a pharmaceutical composition for the treatment of a uterine infection, the composition comprising as an active ingredient an amount of at least one casein peptide, the amount being effective to treat uterine infection in a female mammalian animal.

Finally, in accordance with an additional aspect, the present disclosure provides a kit comprising at least one casein peptide and instructions for use the casein peptide for the treatment of a uterine infection in a female mammalian animal.

DETAILED DESCRIPTION OF THE
INVENTION

The present invention is based on the finding that casein peptides, and in particular, casein hydrolysate can be used for the treatment of uterine infections. Specifically it was found that administration of casein hydrolysate to postpartum cows was effective in the treatment of clinical metritis.

The uterus of mammalian animals, such as bovine, is sterile prior to calving. During gestation, the cervix provides a barrier against intra-uterine invasion by pathogens. At calving, a wide range of bacteria enter the uterus via the now open cervix offsetting a cascade of events that culminate in uterine infection, inflammation and, finally, uterine clearance. However, pathogenic bacteria persist in some cows causing uterine disease by preventing physiological uterine involution resulting in sub-fertility. Because reproductive performance is critical for viable dairy production and reproduction of mammals, uterine health in the post-partum period requires substantial medical veterinary attention.

Parturition-conception intervals and thus the pregnancy rates are a critical factor from an economical point of view of livestock and farm management. The ability to maintain an optimum period of parturition-conception intervals of about 12 to 14 month depends on numerous factors including, inter alia, the clinical state of the animal's uterus, which should be completely free of any post-partum related infections.

Metritis, endometritis, and pyometra are common uterus inflammatory diseases, that occur during the postpartum period of livestock and farm animals, mainly in the early postpartum period, and are primarily associated with contamination of the reproductive tract i.e. uterine.

Uterine infections, and retarded uterine and cervical involution causes economic losses due to costs for treatment, milk withdrawal, reduced reproductive performance, and premature culling.

A wide variety of therapies for endometritis have been reported, including mainly antibiotics administered either by systemic or local administration of prostaglandin F2$\alpha$ (PGF2$\alpha$) or estradiol.

The present disclosure provides an alternative treatment for uterine infection. Thus in accordance with the first aspect, the present invention provides a casein peptide for use in the treatment of a uterine infection in a female mammalian animal. As appreciated, while the invention is described in the following detailed description with reference to the casein peptide for use in the treatment of an uterine infection in a female mammalian such as a lactating animal, it is to be understood that also encompassed within the present disclosure therapeutic methods comprising administration of the casein peptide to female mammal animal, as well as to pharmaceutical compositions comprising as an active ingredient an amount of at least one casein peptide, the amount being effective to treat uterine infection; and to the use of a casein peptide for the preparation of a pharmaceutical composition for the treatment of uterine infection in said animals.

Casein is the principle protein in non-human mammal's milk, also found in human mammal's milk known to include the subgroups αS1, αS2, β and κ. Casein is defined according to the amino acid sequences of each of the subgroups αS1, αS2, β and κ (Farrell, Jr. H. M., Jimenez-Flores R., Bleck G. T., Brown E. M., Butler J. E., Creamer L. K., Hicks C. L., Hollar C. M., Ng-Kwai-Hang K. F., Swaisgood H. E. Nomenclature of the Proteins of Cows' Milk—Sixth Revision. J. Dairy Sci., 87:1641-1674 (2004)).

Casein suitable for use in the present invention can be derived from any of a variety of sources, such as, without being limited thereto, the αS1, αS2 and β and κ-casein of any mammal derived milk, including human and non-human animals.

In the context of the present disclosure, when referring to casein, it is to be understood as also including acid casein, salts of casein, phosphorous containing casein and rennet casein. Further, it is to be understood to encompass plant casein analogs. [e.g. as described in U.S. Pat. No. 3,930,058; Kumar, Surinder and Ramachandran, Kolar S. Modified vegetable protein simulating casein].

The term "casein peptide" in its broadest sense refers to peptide fragments or peptido-mimetic products obtained from or corresponding to one or more sections of casein protein. The peptide may include, without being limited thereto, a casein protein breakdown product which occurs when casein protein is cleaved by enzymes or acids to peptide fragments (also known in the art by the term "casein hydrolysate") or may refer to a synthetically produced products, where the casein peptide exhibits at least a therapeutic beneficial effect in treating uterine infection.

The casein peptide may be a single peptide or a mixture of different peptides which may be independently naturally occurring, semi-synthetic, synthetic peptide, phosphor-peptide genetically engineered casein peptides as well as peptido-mimetics of casein peptides.

The modified, synthetic, semi-synthetic or other types of analogs of the naturally occurring casein peptides are at least 75%, at times 85%, 90%, 95% and even 99% identical (in sequence) to a naturally occurring casein peptide when the two sequences are optimally aligned. Further, any non-naturally occurring casein peptide to be used in accordance with the invention should retain at least part of the biological activity of the naturally occurring casein protein.

A casein peptide in accordance with the invention is characterized by a molecular weight of between about 100 to 10,000 Dalton (e.g. between 2 to 100 amino acids) and preferably between about 100 to 7,000 Dalton.

In the context of the present disclosure, a casein peptide also encompasses a casein hydrolysate. A casein hydrolysate is to be understood as the hydrolyzed form of casein (protein), which includes, among others, the active beta-casein-derived peptide known to those versed in the art.

Naturally occurring casein peptides are typically obtained following enzymatic hydrolysis, the enzyme may be any mammal peptidase, such as, without being limited thereto, plasmin, pancreatin, trypsin, chymotrypsin, neutrase, alcalase, pepsine, carboxypeptidase, cathepsin as well as plant peptidase such as, without being limited thereto, papin, bromelain, as well as enzymes from microorganism source. For example, a naturally occurring casein peptide may be the result of plasmin activity on casein subunits β-casein and αs1- and αs2-casein, κ-casein.

In some embodiments, a casein hydrolysate is obtained by cleavage of the casein protein with tryspin.

The casein peptide may also be a synthetic or semi synthetic peptide. A synthetic peptide may be obtained by any methods known in the art of peptide synthesis, including, solid phase peptide synthesis (R. B. Merrifield (1963). "Solid Phase Peptide Synthesis. I. The Synthesis of a Tetrapeptide". J. Am. Chem. Soc. 85 (14): 2149-2154).

A semi-synthetic casein peptide may be obtained by chemical hydrolysis of casein, e.g. by prolonged boiling in a strong acid (acid-HVP) or strong base or using a chemical agent such as Cyanogen bromide (CNBr).

The casein peptide may also be obtained by molecular engineering, e.g. using recombinant DNA, in molecular techniques known in the art.

The casein peptide may also include a chemical modification of a naturally occurring peptide, e.g. where one or more amino acids are deleted, substituted or modified, e.g. by removal of a side group, substitution of a side group or the introduction of a chemical group. Without being limited thereto, the chemical modification may include the following but not exclusive examples: acetylation, acylation, amidation, ADP-ribosylation, glycosylation, GPI anchor formation, covalent attachment of a lipid or lipid derivative, methylation, myristylation, pegylation, prenylation, phosphorylation, ubiquitination, or any similar process. When referring to replacement of an amino acid sequence by another, it is preferable that the replacement is a conservative substitution. For example, one or more amino acid residues within a casein sequence is substituted by another amino acid of a similar polarity or charge. For example, the non-polar (hydrophobic) amino acids include alanine, leucine, isoleucine, valine, proline, phenylalanine, tryptophan and methionine. The polar neutral amino acids include glycine, serine, threonine, cysteine, tyrosine, asparagine, and glutamine. The positively charged (basic) amino acids include arginine, lysine and histidine. The negatively charged (acidic) amino acids include aspartic acid and glutamic acid. Nonetheless, non-conservative substitutions may also take place as long as it does not significantly change the desired (casein like) biological activity of the resulting casein peptide analog.

The casein peptide may also be a peptido-mimetic peptide, such as peptoids and semipeptoids, which are peptide analogs, having, for example, modifications such as, but are not limited to, cyclization, N terminus modification, C terminus modification, peptide bond modification, including, but not limited to, $CH_2$—NH, $CH_2$—S, $CH_2$—S—O, O—C—NH, $CH_2$—O, $CH_2$—$CH_2$, S—C—NH, CH—CH or CF—CH, backbone modification and residue modification (methods for preparing peptido-mimetic compounds may be found in Quantitative Drug Design, C. A. Ramsden Gd., Chapter 17.2, F. Choplin Pergamon Press (1992), which is incorporated by reference as if fully set forth herein).

The casein peptide according to the invention may comprise "L" as well as "D" form residues.

In one embodiment, the casein peptide is a single peptide or mixture of a phosphopeptide, namely, which contains a single phosphorous group or is a phosphorus-enriched peptide. In one embodiment, the casein peptide is any phosphoserine, phosphotyrosine, phosphothreonine, and/or phosphohystidine-enriched casein peptides (casein phosphopeptide, CPP) and monovalent cation phosphocaseinates, such as sodium, potassium, calcium or ammonium phosphocaseinates. In one embodiment, the casein peptide enriched with phosphorous groups is a casein hydrolysate In one embodiment, the casein peptide comprises a motif defined by the amino acid sequence Ser-Ser-Ser-Glu-Glu (SEQ ID NO:1), where one or more Ser residues are optionally phosphorylated. A non-limiting group of casein peptides comprising the phosphorylated motif is provided by SEQ ID Nos: 2-6. The following provides SEQ ID NO:2-6, their source and location (residue numbers) in the casein polypeptide:

SEQ ID NO: 2
RELEELNVPGEIVES(p)LS(p)S(p)S(p)EESITR (location 1-25 in (β-casein)

SEQ ID NO: 3
QMEAESIS(p)S(p)S(p)EEIVPDSVEQK (location 59-79 in αS1-casein)

SEQ ID NO: 4
KNTMEHVS(p)S(p)S(p)EESIISNETYK (location 1-21 in αS2-casein)

SEQ ID NO: 5
KVNELSKNIGS(p)ES(p)TEDQ (location 36-52 in αS1-casein)

SEQ ID NO: 6
PTLNREQLS(p)TS(p)EENSKKTVD (location 12-140 in αS2-casein).

While the amino acid residues of the peptide sequences set forth in SEQ ID NOs:1-6 are all in the "L" isomeric form, residues in the "D" isomeric form can substitute any L-amino acid residue so long as the resulting peptide analog retains at least part of the biological activity of the corresponding "L" isomer. One reason for designing casein peptides comprising at least one D-amino acid is to increase stability of the peptide to proteolytic degradation.

As indicated above, the casein peptide is used to treat uterine infection. The term "uterine infection" is used herein to denote a pathological condition caused by an influx of pathogens into the mammalian animal's uterine and thereby inflammation of the walls of the uterine. In one embodiment, the uterine infection is a pathogen induced inflammation, also known by the term non-sterile inflammation.

Metritis, either 'puerperal' or 'clinical'; Endometritis, either clinical or sub-clinical; and Pyometra are common uterus inflammatory infectious diseases that occur mainly during the postpartum period of livestock and farm animals, mainly in the early postpartum period, and are primarily associated with contamination of the reproductive tract i.e. uterine.

Metritis is an inflammatory reaction involving all layers of the uterus (endometrial mucosa and submucosa, muscularis, and serosa). Animals with metritis (or perimetritis) have an abnormally enlarged uterus and a purulent uterine discharge detectable in the vagina, more prevalent within 21 days post partum, are usually not systemically septicemic, with overt signs of illness (fever, depression, weakness, and in-appetence).

Puerperal metritis (also referred as toxic puerperal metritis or toxic metritis) is characterized by an abnormally enlarged flaccid uterus and a fetid watery red-brown vulval discharge, associated with acute signs of systemic illness (mostly decreased milk yield, dullness or other signs of toxemia) and fever >39.4° C. usually 10 days after parturition.

Endometritis involves clinical (acute) or sub-clinical inflammation of the uterine. Clinical endometritis is an inflammation of the endometrium only, extending no deeper than the stratum spongiosum, and is characterized by a purulent vulval discharge, (typically up to 42 days postpartum) with no signs of systemic illness. Sub-clinical endometritis may be diagnosed by the presence of more than 18% polymorphonuclear leukocytes in uterine cytology samples and/or by ultrasonographic imaging of fluid in the uterine lumen collected 21-33 days post partum, or the presence of more than 10% of polymorphonuclear leukocytes in uterine cytology samples at 34-47 days after parturation [Sheldon I M, (2006) ibid.].

Pyometra is the accumulation of significant fluid in the uterine lumen in the presence of a persistent corpus luteum and a closed cervix.

Any of the above may be caused by a variety of pathogenic bacteria. In cows, the causative organisms for metritis and endometritis are most often *Arcanobacterium* (*Actinomyces*) *pyogenes*, alone or in association with *Fusobacterium necrophorum* or other gram-negative anaerobic organisms. In some forms of endometritis the causative agents are *Staphylococcus hyicus* or *Escherichia coli*. In other animals, such as mares, the most common etiologic agent of endometritis is *Streptococcus zooepidemicus*, but several other organisms may be involved, including *Escherichia coli, Pseudomonas aeruginosa*, and *Klebsiella pneumoniae*.

Further, the term "uterine infection" encompasses infection of the cervix and of the vagina, such as, without being limited thereto, cervicitis, an inflammation of the cervix that may be caused by the *bacterium Chlamydia trachomatis*, by *bacterium Neisseria gonorrhoeae* (also called *Gonococcus*); or vaginitis, an inflammation of the vagina, that may be caused by the yeast *Candida albicans*, by the *bacterium Gardnerella* or by the parasitic protozoan *Trichomonas vaginalis*; and vulvitis, an inflammation of the vulva sometimes referred to as vulvovaginitis (because the vulva is also often inflamed when there is inflammation of the vagina).

In some dairy herds, 40% of the postpartum animals are diagnosed with uterine infections and thus are in need for veterinarian treatment (Lewis G. S., Uterine health and disorders. J. Dairy Sci., 80:984-994 (1997)).

Cows diagnosed with uterine infections such as for example metritis or endometritis and retarded uterine and cervical involution, show significant reduction in conception rates, prolonged days to first insemination service as well as increased intervals from calving to breeding which is exemplified by reduced numbers of pregnancies. For example, uterine infections may increase the period between calving to calving, which optimally should not exceed an optimum period of about 12 to 14 months, i.e. around one calving per cow per year. The ability to maintain such an optimum period depends on numerous factors including, inter alia, the clinical state of the animal's uterus, which should be completely free of any post-partum related infections.

Thus, uterine infections cause economic losses such as increased herd health-related costs, often reduce feed consumption, cause an appreciable reduction in milk production, and force breeders and milk providers to cull livestock animals, such as cows, that would otherwise be productive and remain in the herd.

Endometritis and metritis may be treated spontaneously and normally there will be no appreciable effect on reproductive performance or any other measure of productivity.

As appreciated, when a uterus becomes infected it may significantly affect milk production.

The invention is applicable for a variety of female mammalian animals, which may be either before a lactating stage (e.g. heifers) or a lactating animal.

In some preferred embodiments, the female mammalian animal is a non-human mammalian. Possible non-human mammalian animals in the context of the invention may be selected from the non-limiting group consisting of a dog, a sheep, a goat, a sow, a cow, a zebu, a zebra, a cat, a donkey, an ass, a buffalo, an oxen, a mare (including a filly), a reindeer, a yak, a camel, a lama, an alpaca, an elephant, a pig, a boar, and a warthog. In one embodiment, the invention is applicable to lactating animals.

In yet another embodiment, the invention relates to livestock lactating animals, including, without being limited thereto, cows, buffalos, goats, sheep, mare, zebus, sows and oxen. A lactating animal of particular interest is a cow.

The mammalian animal may be any of nulliparous, primiparous or multiparous lactating animal. A "nulliparous" ("nullipara" or "para") is to be understood as referring to an animal that has never completed a gestation period; a "primiparous" ("primipara" or "primip") is to be understood as referring to an animal that has given birth to at least one offspring (a single parturition); and a "multiparous" ("multip") is to be understood as referring to an animal that has experienced two or more parturitions.

In one embodiment, the uterine infection is at any stage before calving, e.g. in a heifer, as well as between two consecutive calvings.

In yet a further embodiment, the uterine infection is a post-partum infection. In the context of the present invention, the term post-partum infection refers to infections occurring at any time after parturition, e.g. at the time interval between two consecutive parturitions and at some embodiments, at a time after parturition until the beginning of estrus. In some embodiments, the post partum period is considered to be during the first 7 weeks after parturition.

The casein peptide is used to treat any of the above uterine infections. The term "treatment" or "treating" and the like are used herein to refer to obtaining a desired pharmacological and physiological effect on the female mammalian animal having or in disposition of developing an uterine infection (e.g. being in post partum period). As such, the effect may be prophylactic in terms of "preventing" or partially preventing an infection, symptoms or conditions thereof in a lactating animal in predisposition of developing an uterine infection and/or may be therapeutic in terms of partial or complete cure of an already existing infection, condition, symptom or adverse effect attributed to the infection. Thus, the term "treatment", as used herein, covers any of the following (a) preventing the infection from occurring in a female mammalian animal which may be predisposed to the infection (e.g. before as well as after calving) but has not yet been diagnosed as having it, e.g. the clinical symptoms of the infection have not yet being developed to a detectable level; (b) inhibiting the infection, i.e., arresting or reducing the development of the infection or its clinical symptoms such as inflammation and/or fever; or (c) relieving the infection, i.e., causing regression of the infection and/or its symptoms or conditions.

In some embodiments, treatment comprises parenteral (e.g. injection, infusion or the like) and/or topical administration of said at least one casein peptide. The administration may be intrauterine and/or vaginal administration. In one embodiment, the administration is transcervical intrauterine administration.

Depending on the route of administration, the at least one casein peptide may be formulated with a suitable acceptable carrier to form a pharmaceutical composition. An acceptable carrier is a pharmaceutically and physiologically acceptable carrier and is to be understood as a carrier or an excipient that is generally safe, non-toxic and neither biologically nor otherwise undesirable. A pharmaceutically acceptable carrier as used in the specification and claims includes either one or more than one of such carriers. The carrier can be any of those conventionally used and is limited only by chemicophysical considerations, such as solubility and lack of reactivity with the at least one casein peptide, and by the route of administration.

As appreciated by those versed in the art, treatment may also include combined administration with other drugs, such as other antibiotics.

The pharmaceutical composition may also include other additive to give form or consistency to the composition or to increase stability, sterility and isotonicity of the composition or to enhance uptake of the casein peptide across membranes. For example, the additive may include a pH adjusting agent, e.g. to maintain the pH of the composition in the range of 6 to 8, or even at times in the range of 6.7 to 6.9 which was found to be the most suitable pH for topical or parenteral administration of casein peptides.

In one embodiment, the amount of the at least one casein peptide effective to achieve treatment of uterine infection is between 10 ng/ml to 500 mg/ml per administration dose, at times, between 10 ng/ml to 200 mg/ml per administration dose and even at times 10 ng/ml to 100 mg/ml per administration dose. In some embodiments, the casein peptide is a casein hydrolyste comprising a mixture of casein peptides, at least a portion of which being therapeutically effective to treat the uterine infection. At times, the casein peptide may be administered in a non-solution form (e.g. cream), in which case, the amount will be between about 10 ng/kg body weight to 200 mg/kg body weight per administration dose, at times, between about 10 ng/kg body weight to 100 mg/kg body weight per administration dose. An administration dose refers to a single administration event, i.e. an animal may receive a single administration dose or several administration doses per day, or during two or more days.

In one embodiment, the at least one casein peptide is administered once (single dose administration). In some other embodiments, two or more administrations of said at least one casein peptide are executed, typically between 2 to 6 doses. When more than one dose of the at least one peptide is administered, it is typically (albeit not limited thereto) that a time interval of from 2 hours to 14 days is used between two consecutive administrations. Notwithstanding the number of administrations, it is in accordance with one embodiment that the single or first administration is after calving, typically up to 120 days post calving, more particularly, up to 70 days post calving, further at times up to 30 days post calving, and at times immediately post calving (i.e. minutes or hours after calving) as well as up to day 26 post calving.

As used herein, the forms "a", "an" and "the" include singular as well as plural references unless the context clearly dictates otherwise. For example, the term "a casein peptide" includes one or more such peptides, e.g. mixture of peptides which are effective in treating uterine infection.

Further, as used herein, the term "comprising" is intended to mean that the composition include the recited one or more peptides, i.e. the at least one casein peptide (which may by itself relate to a preparation comprising a mixture of such peptides), but not excluding other elements, such as physiologically acceptable carriers and excipients as well as other active agents. The term "consisting essentially of" is used to define compositions which include the recited elements but exclude other elements that may have an essential significance on treatment of uterine infection. "Consisting of" shall thus mean excluding more than trace elements of other elements Embodiments defined by each of these transition terms are within the scope of this invention.

Further, all numerical values, e.g. when referring the amounts or ranges of the elements constituting the composition comprising the at least one casein peptide as an active ingredient, are approximations which are varied (+) or (−) by up to 20%, at times by up to 10% of the stated values. It is to be understood, even if not always explicitly stated that all numerical designations are preceded by the term "about".

The invention will now be exemplified in the following description of experiments that are carried out in accordance with the invention. It is to be understood that these examples are intended to be in the nature of illustration rather than of limitation. Obviously, many modifications and variations of these examples are possible in light of the above teaching. It is therefore, to be understood that within the scope of the appended claims, the invention may be practiced otherwise, in a myriad of possible ways, than as specifically described hereinbelow.

The following examples are presented in order to more fully illustrate the preferred embodiments of the invention. They should in no way be construed, however, as limiting the broad scope of the invention since numerous modifications and variations therein will be apparent to those skilled in the art.

DESCRIPTION OF SOME NON-LIMITING EXAMPLES

Materials

Propidium iodide (solution for fluorescence, CAS 25535-16-4, Sigma-Aldrich catalogue 70335, Sigma-Aldrich Co., 3300 South 2nd Street, St. Louis, Mo. 63118).

Recombinant human IL-8 (rhIL-8) (ProSpec-Tany TechnoGene Ltd., Rehovot Science Park, P. O. Box 398, Rehovot 76103, Israel).

Isotonic Percoll (based Percoll® Sigma-Aldrich catalogue P4937, Sigma-Aldrich Co., 3300 South 2nd Street, St. Louis, Mo. 63118).

Non-viable *Streptococcus zooepidemicus* suspension (Omnisorbin, Calbiochem, Bad Soden, Germany).

Oxytetracycline dehydrate 200 mg/mL (Alamycim®, Norbrook Laboratory Ltd, UK).

Water for irrigation (Cure Medical, Teva Medical, Israel). In the following, also, the cows are Israeli Holstein-Friesian dairy cows.

Phorbol myristate acetate (PMA, Sigma-Aldrich catalogue P8139, Sigma-Aldrich Co., 3300 South 2nd Street, St. Louis, Mo. 63118).

Nonfluorescent dye dihydrorhodamin 123 (DHR 123, Morbitec, Göttingen, Germany).

Example 1—Preparation of Casein Hydrolysate

Preparation of Stock Solutions: 25 mM Tris HCl at pH=8.0 (20 Liters) and 25 mM Tris HCl at pH=7.0 (5 Liters).

Tris base (Applichem GmBH, Darmstadt, Germany) was weighted (75.687 gr) and dissolved in a glass bottle equipped with magnetic stirring bar containing 24 liters of water for irrigation (WFI, Cure Medical, manufactured by Teva Medical, Israel), at a final pH of about 11.5, until clarification.

To the 19 liter solution, the pH was adjusted to about 7.5-8.5 (preferably about 8) using 10N HCl (Sigma-Aldrich, Israel) and the volume was finalized to 20 liter by adding WFI. To the 4.75 liter solution, the pH was adjusted to between about 6.75-7.25 (preferably 7.0) and the final volume was finalized to 5 liter by adding WFI. The solutions were stored at room temperature until further use.

Preparation of Casein-Derived Peptides:

Casein hydrolysate was prepared by Biological Industries Israel (Beit Haemek Ltd., Israel) according to the following:

Tris HCl 25 mM, at pH=8.0 (20 liters) were added into a glass bottle and the temperature was adjusted to between about 40° C. to 48° C., preferably 45° C.

A total of 4,000 gr sodium caseinate (DMV International. FrieslandCampina Central Office, Amersfoort, The Netherlands) were added into the Tris HCl solution to obtain a 20% (w/v) solution. The mixture was stirred gently to reachfull dissolution. The solution pH was maintained at about 8.0 and the temperature at about 45° C. Then 4 g of porcine trypsin powder (Sigma-Aldrich, Israel) were added to the solution. The mixture was gently stirred on a magnetic stirrer or deflocculating (preferred) stirrer under gentle agitation at about 45° C. The hydrolysis was allowed to proceed for a total of about one hour. The pH was then adjusted to about pH 8.0 using 10N NaOH (J T Baker, Avantor Performance Materials, Phillipsburg, N.J., U.S.A.) and the temperature was maintained at about 45° C.

The trypsin in the crude hydrolysate was inactivated by elevating the temperature to 90° C.-95° C. for one hour. The supernatant was cooled to room-temperature by using ice in an external bath. The pH was adjusted to 4.7 using 10N HCl. After 15-30 minutes, the insoluble material was removed by centrifugation for 20 min, at 2-8° C., 4500 rpm.

The supernatant was transferred to a new sterile glass bottle and the pH was adjusted to 7.0 using 10N NaOH.

The solution volume was adjusted to 20 liters by adding the 25 mM Tris HCl solution at pH 7.0.

The final volume was filtered sequentially through 1.2 µm/0.65 µm pre-filters and through two 0.45/0.22 µm sterile CA membrane filter capsules. The filtered solution was transferred to glass serum bottle (100 ml and 200 ml respectively) by aseptic filling in sterile bench. The samples were stored at −20° C. (frozen) until further use.

The product (raw material) comprised 20% Sodium Caseinate, 25 mM Tris-HCl and 0.02% Trypsin.

Example 2: Clinical Study 1—Low Dose Studies of the Effect of Casein Hydrolysate in Acute Post-Partum Bovine Clinical-Metritis The effects of bovine casein hydrolysate in comparison with antibiotic drugs, was studied in dairy cows suffering from acute puerperal metritis (Sheldon et al., ibid 2006).

General Study Information:

The cows recruited for this study were lactating Holstein Friesian located in large dairy herd in Israel (longitude 34°40'E-35°30'E; latitude 30°30'N-33°01'N). The cows were milked 3 times a day. The herd used was free-stall barn with a size ranged from 300 to 350 milking cows.

At dairy farm an administrating veterinarian was selected and appointed by the Clinical Research Organization (CRO) (Hachaklait—Israeli Cattle Breeders Association, Caesaria Industrial Park, Israel) in order to carry out the study functions, specifically the administrating veterinarian was responsible for treatment administration, clinical assessment, training dairy herd personal, proper storage, perform necessary clinical observations for adverse event assessment and fill report forms. All study documents were filled out legibly in indelible black/blue ink. The original data were sent to the sponsor.

Physical Observations:

All dairy cows were routinely examined in the first 5 to 10 days postpartum and their physical condition was assessed using measures of:
- (i) status of the uterus by trans-rectal palpation;
- (ii) heart girth measurements for approximate weight determination;
- (iii) a body condition score provided by the veterinarian, which is based on the cow's height and fat composition in various parts of the body according to Edmonson A. J., et al. [Edmonson A. J., Lean I. J., Weaver L. D., Farver T., Webster G. A body condition scoring chart for Holstein dairy cows. *J. Dairy Sci.*, (1989); 72:68-78].

Cows are enrolled to the study provided that their physical condition is complied with the inclusion criteria as follows:
- Cows with clinical postpartum metritis,
- Cows with non-twins delivery,
- Cows were not administered with intrauterine or systemic reproductive hormone therapy during the last 4 weeks,
- Cows with no diagnosed morbidities, which may be potentially influence the outcome of treatment in the judgment of the investigator,
- The herd managers agreed not to administer any intrauterine or reproductive hormonal therapy before examination of cows for this trial.

In addition, cows were enrolled to the clinical study provided that they have none of the following characteristics (herein "exclusion criteria"):
- Cows had abnormal internal genitalia (including adhesions)
- Cows with diagnosis and or treatment of severe vaginitis, lameness, mastitis-ketosis and digestive disorders during the current post calving period or any other clinical disease requiring systemic treatment at enrollment,
- Cows identified to be culled (not to be inseminated) after calving
- Cows administrated with immunotherapy within 3 weeks prior to study entry,
- Cows administrated with anti-inflammatory and/or anabolic therapies, either systemic or by feeding 2 weeks prior to study entry.
- Cows which are suspected or with a diagnosis of retained fetal membranes at the time of the current calving.
- Cows which are suspected or with a clinical evidence of acute puerperal metritis with a systemic effect
- Cows which are indented to be removed for any reason from the farm in the current location.

Cows in a proper physical condition (as defined above in the inclusion criteria and the exclusion criteria), that were diagnosed with confirmed clinical metritis, as determined by any one of the following clinical criteria, were enrolled to this clinical study:
1) cows must be febrile (i.e., morning rectal temperature more than 39.4° C.) and/or
2) cows must have a flaccid, non-retractable uterus that is located in the abdomen, a cervical diameter >7.5 cm, and a watery, mucopurulent, or fetid vulvar discharge.

Study Specifics:

On day "0" (first day of the study), dairy heifers or primiparous or multiparous dairy cows from the same herd and within the same lactation and ages were randomly divided, using tables prepared in advance by the investigator, to receive one or other of the treatments. Within each table, cows were assigned to treatment in pairs, a cow for each group.

Treatment:

Case study Arm ("arm 1")—450 mg of bovine casine hydrolysate (Batch Number B100) administered in a 150 ml solution until completion of the arm's sample size.

Control Arm ("arm 2")—25 ml of Oxytetracycline dehydrate (200 mg/ml total of 5,000 mg) (Norbrook Laboratory, UK).

No other intrauterine treatments were provided to the tested cows (including but not limited to intrauterine antimicrobials, internal or external teat systemic antimicrobials).

Treatment was initiated at day "0" and was administered to the cows through transcervical intrauterine infusion using a sterile uterine catheter.

All the experiments were blind case-control studies as all unidentified administered products were labeled in vials of bovine casein hydrolysate and the negative control was always administered to cows by the same route as the treatment, thus the investigators or herdspersons or veterinarian was unable to identify the study cases or the controls.

Study Endpoints:

The end points of this study were safety and efficacy as detailed below.

Safety:

Determining maximum severity of any toxicity probably related to bovine casein hydrolysate with the current dose.

Determining maximum severity of any toxicity possibly related to bovine casein hydrolysate with the current dose.

Safety was determined by monitoring on days 0.3, 1, 2, 3, 7 and 14 post-treatment, the appearance of adverse events (as detailed below) or any sign of toxicity.

In addition, the overall general impression from each cow was assessed and ranked according to the description on Table 1.

TABLE 1

Ranking of cow's general impression

| Score | Description |
|---|---|
| 0 | Normal |
| 1 | Slightly depressed |
| 2 | Depressed (solitude, head leaning down) |

The program manager/monitor/sponsor was responsible to immediately notify on any possible signs of AEs. Appropriate actions may involve locating and breaking blinding codes so that appropriate medical treatment can be given, recording of the AEs in the study documentation, and reporting AEs to the sponsor.

According to veterinary criteria if adverse events were encountered (including in the lapse time of the first post treatment visit) or significant signs and symptoms of clinical post-partum metritis were observed at day 7 post treatment, same treatment as provided in day 0 was administrated to the cow.

All serious and/or unexpected adverse events were documented.

Efficacy:

Treatment success was measured by the average reduction of the following two parameters:

if the animal group had an average rectal temperature reduction at day 14 post treatment compared to the average temperature measured during day 0 and/or;

if the animal group had an average reduction in the discharge parameters at day 14 post treatment.

Efficacy was assessed by measuring the rectal temperature; genital system morphology and the genital secretions at a first visit after the morning observation and milking, before the treatment, 6-8 hours after the treatment and then on days 1, 2, 3, 7 and 14 post treatment. In general, treatment success was assessed after a total of 14 days after treatment.

The administrated veterinarian examined all cows and was in charge on the ranking of the genital secretions, from 1 to 4, based on the descriptions provided in Table 2.

TABLE 2

Ranking of genital system secretion

| Score | Description |
|---|---|
| 0 | None. |
| 1 | Transparent thin secretion |
| 2 | Thin serosanguinotic secretion |
| 3 | Mucopurulent secretion |
| 4 | Purulent secretion with foul smell |

The genital system morphology was assessed and ranked according to the description in Table 3.

TABLE 3

Ranking of genital system morphology

| Score | Description |
|---|---|
| 0 | Normal appearance of the vulva and vagina, no apparent redness, swelling, sign of local pain or signs of inflammation |
| 1 | Mild redness and swelling |
| 2 | Severe serosanguinotic secretion, swelling and/or injuries |

Post Treatment Cow Management

Generally, post-treatment animal management and observation schedules were be followed according to the specific facility's practice. Following treatment, study cows have been commingled with non-study cows and will be housed in accordance with each site's standard practices. All cows have been subjected to the same basic management (including housing and rations, the timing of changes in housing or ration, and any vaccination protocols, exclusive of vaccination against metritis pathogens if such are available Preparation and Storage of Materials for the Study:

Bovine Casein Hydrolysate:

After manufacture, bovine casein hydrolysate was immediately frozen to reach a temperature between −15 to −20° C. This process was done in less than 16 hours from manufacture process. As described above, 155 ml casein hydrolysate was filled in vials of 200 ml, out of which 150 ml were injected (the rest 5 ml were kept for follow up).

Package vials containing the bovine casein hydrolysate were transported from the manufacture facility to the participating dairy herds through Cold Transport Delivery (Frozen) and were stored at each dairy herd in a designated freezer (−20° C.)

One day before (24-36 hours) the scheduled treatment day (after the morning milking), vials containing the biologic products were taken out of the freezer and kept in a cooling refrigerator's temperature (4-8° C.) until the time of administration.

At any case that the content of a vial containing the bovine casein hydrolysate was not administrated, the vial was stored in the original package, marked 000, and was not administrated at any time.

Antibiotics were kept refrigerated (4-8° C.), to avoid prolonged exposure to moisture and direct sunlight.

Results—Clinical Study 1—Low Dose Study

Randomized blind safety studies were conducted on a total of 16 cows, eight cows were administered with casein hydrolysate (treatment, arm 1) and eight cows were administered with antibiotics (control, arm 2).

All tested cows had a normal behavior during the 14 days post treatment, specifically the general impression from each cow was ranked as "0" in Table 1 following treatment administration with none of the cows showing any signs of depression, less food intake.

Treatment efficacy was measured, at the indicated times after the treatment administration, by measuring the fever of each cow and by monitoring the genital system secretion and morphology. The secretions and morphology for each cow were ranked according to the description in Table 2 and in Table 3, respectively.

Comparison of the results obtained from cows treated with casein hydrolysate (150 ml) and from cows treated with antibiotics indicated that casein was able to maintain the same body temperature as antibiotics (Table 4).

TABLE 4

Effect of casein on the cow's fever

| Time of measurement | Bovine Casein Hydrolysate (° C.) | Antibiotics (° C.) |
|---|---|---|
| Before treatment (day = 0) | 38.8 ± 0.57 | 38.8 ± 0.26 |
| 6-8 h after treatment | 39.4 ± 0.54 | 39.4 ± 0.66 |
| Day 1 (22-32 h after treatment) | 39.0 ± 0.49 | 39.1 ± 0.27 |
| Day 2 | 39.2 ± 0.40 | 39.1 ± 0.47 |
| Day 3 | 38.8 ± 0.42 | 38.9 ± 0.37 |
| Day 7 | 38.8 ± 0.44 | 38.9 ± 0.18 |
| Day 14 | 38.8 ± 0.33 | 38.8 ± 0.41 |

The genital system morphology of all the treated cows was found to be normal, and ranked "0" with no appearance of redness or swelling as described in Table 3, meaning there were no local adverse events.

In addition, it was observed that the treatment of the cows with casein hydrolysate for 14 days reduced the genital secretions by about 50% similarly as antibiotics (Table 5).

TABLE 5

Effect of casein on genital secretions

| Time of measurement | Bovine Casein Hydrolysate (ranking) | Antibiotics (ranking) |
|---|---|---|
| Before treatment (day = 0) | 3.875 ± 0.353 | 3.625 ± 0.517 |
| 6-8 h after treatment | 3.75 ± 0.462 | 3.0 ± 0.92 |
| Day 1 (22-32 h after treatment) | 3.75 ± 0.462 | 2.12 ± 0.84 |
| Day 2 | 3.25 ± 1.03 | 2.0 ± 0.92 |
| Day 3 | 3.25 ± 1.03 | 2.0 ± 0.92 |
| Day 7 | 3.0 ± 0.92 | 1.5 ± 0.75 |
| Day 14 | 2.0 ± 1.09 | 1.5 ± 0.75 |

The results described above and relating to Tables 1 to 5 clearly show the following:

administration of bovine casein hydrolysate to cows at a dose of 450 mg, was not toxic and did not cause any local adverse effects and systemic adverse effect and therefore may be safely intrauterine administered to cows.

In terms of efficacy, as shown in the fever measurements as well as in the genital morphology and genital secretions measurements, administration of 450 mg bovine casein hydrolysate was found to be as efficient as the common metritis treatment, antibiotics, in treating postpartum clinical metritis.

The above results provide evidence for the beneficial therapeutic advantage of using casein peptide over standard antibiotics, at least for the following reasons: casein is a natural material against which resistance would typically not be developed (as opposed to antibiotics), and further, since casein is a natural material the milk milked from the animal during casein peptide treatment may be used (and not discarded, as done with antibiotics-treated lactating animals).

Example 3: Clinical Study 2—High Dose Studies of the Effect of Casein Hydrolysate in Acute Post-Partum Bovine Clinical-Metritis The cows recruited for this study were lactating Israel Holstein Friesian located in a large dairy herd in Israel (longitude 34°40'E-35°30'E; latitude 30°30'N-33°01'N).

Cows enrollment to the study with respect to the physical conditions, inclusion criteria and exclusion criteria were as detailed above for clinical study-1 with respect to the overall physical condition and with respect to the diagnosis with clinical post partum metritis. In addition, cows randomization was as detailed above.

On day "0" (first day of the study) dairy heifers or primiparous or multiparous dairy cows from the same herd and with the same lactation and ages were randomly divided, using tables prepared in advance by the investigator, to receive one or other of the treatments. Within each table, cows were assigned to treatment in pairs, a cow for each group.

Treatment:
Case study Arm ("arm 1")—1350 mg of bovine casein hydrolysate (Batch Number B100) administered in a 150 ml solution 3 times.
Control Arm ("arm 2")—25 ml of Oxytetracycline dehydrate (200 mg/ml total of 5,000 mg) (Norbrook Laboratory, UK).

No other intrauterine treatments were provided to the tested cows (including but not limited to intrauterine antimicrobials, internal or external teat systemic antimicrobials).

Treatment was initiated at day "0" and was administered to the cows through transcervical intrauterine infusion using a sterile uterine catheter.

All the experiments were blind case-control studies as all unidentified administered products were labeled in vials of bovine casein hydrolysate and the negative control was always administered to cows by the same route as the treatment, thus the investigators or herdspersons or veterinarian was unable to identify the study cases or the controls.

Study Endpoints:
Safety and efficacy criteria are as detailed above for clinical study 1 (Example 2)

The administered veterinarian examined all cows and was in charge on the ranking of the genital secretions, from 1 to 4, based on the descriptions provided in Table 2 of clinical study 1 as well as the genital system morphology according to the description in Table 3 of clinical study 1 and the overall general impression from each cow according to the description on Table 3 of clinical study 1.

In addition, the veterinarian aseptically will prepare the genital area, specifically the vulva to perform uterine swabs's samples and to obtain uterine cytology samples from the designated cows. Uterine swab samples are taken from the uterine body and are obtained by using protection sterile uterine swabs.

Uterine swab samples for uterine cytology samples are obtained before the treatment and on days 7 and 14 post treatments.

Prior to swab sampling, labeling of samples' slide is done and includes Cow ID and indication, date of indication, Site ID and Date and Time of Sampling. Additional submission forms are filled according to laboratory instructions.

Swabs after being sampled are rolled on a designated glass slide in a clean environment. The rolled process starts from the label side (white) to the end of the slide and is repeated twice or three times. Biological samples should not be included in both extremes parts of the slide. Each sample slide is immediately placed separately in a transport medium and transfer to the laboratory at 4° C.-8° C. within three (3) hours after collection. Immediately upon receipt, uterine swabs are re-suspended in 2 ml thioglycolic broth that is partly diluted 100 times by adding more broth.

All uterine samples are analyzed for pathology, for example, for the presence of neutrophils, lymphocytes, basophiles, macrophages, eosinophils.

Also, on day 14, the presence of infection after uterine swabs sample performed during pre-treatment and post-treatment (day 14) is monitored.

In addition uterine swab sample are performed after 7 and 14 days as described above and on day 14, assessment of any adverse event was done as detailed above.

Efficacy in this experiment is measured by parameters associated with the ability to prevent uterine infections in non-retained fetal membrane animal as follows:

(i) Microorganism parameters: clinical and bacteriological negative rates after treatment compared to control (main parameters). Generally, bacteria is categorized, according to known pathogenicity within the uterus (Sheldon I. M., Noakes D. E., Rycroft A. N., Dobsons H. Effect of intrauterine administration of oestradiol on postpartum uterine bacterial infection in cattle. Animal Reproduction Science, 81:13-23 (2004)). The categories vary from 1 to 3 based in clinical endometritis, which correspond to:

Category 1—bacteria that frequently cause metritis;
Category 2—bacteria that are an infrequent cause of metritis; and
Category 3—bacteria not recognized as uterine pathogens.

Bacterial growth scores are summed-up for all bacteria (total bacterial score) or for each of the pathogen categories (1-3).

(ii) Biological status: by measuring artificial insemination performance, pregnancy hazard and milk yield (main parameters).

According to Veterinary criteria if adverse event were encountered (including in the lapse time of the first post treatment visit) or significant signs and symptoms of clinical post-partum metritis, same treatment was administrated to the cow (bovine casein hydrolysate to cases and antibiotics to controls). All study documents were filled out legibly in indelible black/blue ink. The original data were sent to the sponsor.

Post treatment management was as detailed above in clinical study 1.

The materials were prepared and stored as detailed above in clinical study 1.
Results—Clinical Study 2—Efficacy Study:

Randomized blind safety studies were conducted on a total of 7 cows, 4 cows were administered with casein hydrolysate (treatment, arm 1) and 3 cows were administered with antibiotics (control, arm 2).

No adverse effects were observed in any of the cows treated for 14 days with casein hydrolysate, specifically the general impression from each cow indicated that the cow behavior was normal during the 14 days post treatment, specifically the general impression from each cow was ranked as "0" in Table 1, following treatment administration, with none of the cows showing any signs of depression or less food intake.

The genital system morphology of all the treated cows was found to be normal, and ranked "0" with no appearance of redness or swelling as described in Table 3 in clinical study 1 above, meaning there were no local adverse events.

Comparison of the results obtained from cows treated with casein hydrolysate (450 ml) and from cows treated with antibiotics indicated that casein was able to prevent increase in body temperature to an extent similar to that obtained with antibiotics (Table 6).

TABLE 6

Effect of casein on the cow's fever

| Time of measurement | Casein Hydrolysate (° C.) | Antibiotics (° C.) |
| --- | --- | --- |
| Before treatment (day = 0) | 38.9 | 38.4 |
| 6-8 h after treatment | 38.6 | 39.1 |
| Day 1 (22-32 h after treatment) | 38.7 | 38.6 |
| Day 2 | 38.1 | 38.4 |
| Day 3 | 38.4 | 38.9 |
| Day 7 | 38.6 | 38.3 |
| Day 14 | 38.8 | 38.7 |

The results show that treatment of casein hydrolysate is effective, similar to antibiotics and no adverse events were observed, even at high dose treatment.

Examinations, Inclusion and Exclusion Criteria for Examples 4-8
Routine Examination of the Cows Dairy cows are routinely examined immediately after calving to assess their physical conditions using measures of:

(i) status of the uterus by trans-rectal palpation and ultrasonograph;

(ii) heart girth measurements for approximate weight determination;

(iii) a body condition score provided by the Veterinarian, which is based on the cow's height and fat composition in various parts of the body according to Edmonson A. J., et al. (Edmonson A. J., Lean I. J., Weaver L. D., Farver T., Webster G. A body condition scoring chart for Holstein dairy cows. J. Dairy Sci., 72:68-78 (1989).

Cows which are diagnosed with postpartum health abnormalities, for example ketosis, retained placenta, left displays abomasums, lameness, are provided with appropriate medical treatment and are excluded from any future study trial.
General Examination Protocol (Examples 4-8):

In all in vivo experiments described below, the tested population includes about 25% dairy heifers or primiparous and about 75% multiparous dairy cows (at post partum period). Dairy cows from the same herd and with the same lactation and age are randomly distributed within the different study groups. In addition, all experiments are blind case-control studies as all unidentified products to be administrated are labeled in vials of bovine casein hydrolysate and the negative control is always administered to cows by the same route as the treatment, thus the investigators or herdspersons is unable to identify the study cases or the controls. Unless otherwise indicated all treatments (including saline) are administered by transcervical intrauterine infusion.

Cows and heifer calving during the study period will be included in this trial. All cows will be examined with respect to following inclusion criteria and exclusion criteria.

The inclusion criteria for participation in the study are:
 Cows with a normal health uteri (only for example numbers 4 and 5),
 Cows with a uterine infection (for examples 6, 7 and 8),
 Cows with non-twins delivery,
 Cows not being administered with intrauterine or systemic reproductive hormone therapy in the current lactation,
 Cows not diagnosed with morbidities, which may be considered to potentially influence the outcome of treatment in the judgment of the investigator,
 Herd managers agreed not to administer any intrauterine or reproductive hormonal therapy before examination of cows for this trial.

The exclusion criteria for not participation in this study are:
 Cows with an abnormal internal genitalia (including adhesions),
 Cows diagnosed with and or treated to severe vaginitis, retained fetal membrane history, lameness, mastitis, ketosis and digestive disorders during the current post calving period or any other clinical disease requiring systemic treatment at enrollment,
 Cows identified to be culled (not to be inseminated) after calving,
 Cows administered with immunotherapy within 3 weeks prior to study entry,
 Cows administered with anti-inflammatory and anabolic therapies, either systemic or by feeding within 2 weeks prior to study entry.

Example 4—Clinical Study 3—Studies of the Effect of Bovine Casein Hydrolysate in Reproductive Performance of Dairy Cows The goal of this study is to evaluate the effect of bovine casein hydrolysate treatment post partum on reproductive performance of dairy cows; the effect of intra uterin infusion of casein hydrolysate on the cow's reproductive performance which will be compared to control.

Study will be considered successful provided that at an average period of 49-70 days postpartum, one or both of the following criteria is achieved in the bovine casein hydrolysate treated cows:

(1) the artificial insemination submission rate is at least 5% higher, preferably 10% higher, most preferably 20% higher compared to controls; and/or (2) the open days (calve to breeding) are shorter at about 5-9 days, preferably 10 days or more compared to controls or that a statistically significant result is achieved in the difference of the open days between cases and controls Following the clinical examination, recruited dairy cows will be blinded assigned within herd after calving to the different study groups, i.e. bovine casein hydrolysate treated cows and control cows. Cows will be randomly assigned to the two groups.

Treatment:
Treated cows—will be administered by an i.u infusion bovine casein hydrolysate.
Control cows—will be administered by an i.u infusion control solution Each animal will be reexamined biweekly after recruitment similar as at enrollment up to day 40-60 post calving.

After the voluntary waiting period, of about 42 days, cows will be subjected to a synchronization of ovulation and timed insemination protocol for the first service. Pregnancy diagnosis will be conducted by palpation per rectum of the uterus and its contents at about 42 to 49 d after insemination.

Insemination dates will be collected using on-farm data-recording forms and data records. Reproductive performance on individual animals will be collected for a minimum of 2 months after enrollment. Observations of time to pregnancy will be censored.

The following descriptive outcomes will be measured to assess reproductive performance:
interval from calving to first insemination (days to first service),
first service pregnancy (%),
interval from calving to pregnancy (day open),
number of inseminations for pregnant cows,
removal risk for reproductive failure (%),
milk yield (liters per day), Observations of time to pregnancy for cows that will be culled during the trial before pregnancy will be censored on the date of culling. For cows that will be not pregnant at the termination of data collection, observations will be censored on the last date.

Example 5: In Vivo Prophylaxis of Postpartum Uterine Infections in Dairy Cows

The effects of bovine casein hydrolysate on systemic preventive treatment of metritis and endometritis (clinical and subclinical) will be evaluated in dairy cattle (Sheldon I. M., Lewis G. S., LeBlanc S., Gilbert R. O. Defining postpartum uterine disease in cattle. Theriogenology, 65:1516-1530 (2006)).

The goal of this study is to evaluate the efficacy of a preventive treatment of cows from uteri infectious with an administration of bovine casein hydrolysate. Specifically, to prevent metritis and endometritis (clinical and subclinical) after an intrauterine infusion of bovine casein hydrolysate in cows, administered after calving regardless of their body temperature.

The objective of this study is to prevent the occurrence of uterine infection or to minimize its effects after it has occurred after a blanket preventive treatment to be carried post-partum by intra uterine infusion of bovine casein hydrolysate in dairy cows and heifers without retained fetal membrane compared to controls.

During enrollment the following examinations will be held:
(i) a general physical examination and a clinical examination performed on the reproductive tract by transrectal palpation as well as rectal fever measurements, respiratory evaluation and heart beat measurements.
(ii) uterine bacteriology examination—uterine bacteriology samples cells are obtained for determination of endometrial bacteriological status by the presence of microorganism (infections). After calving, the cows are assigned into two study groups. a bovine casein hydrolysate (administered by intra uterine infusion) (Group I), and control (Group II).

In addition, for all clinical evaluations, the treatment is performed also in cows without retained fetal membrane and regardless of the cow's body temperature.

Treatment follow up is performed on biweekly basis examinations including similar examinations as in the enrollment—treatment stage. Finally, on day 42 post treatment, endometrial (bacteriology) examination as well as clinical examination are performed to evaluate the presence or absence of uterine infections.

Efficacy in this experiment is measured by parameters associated with the ability to prevent uterine infections in non-retained fetal membrane animal as follows:

(i) Microorganism parameters: clinical and bacteriological negative rates after treatment compared to control (main parameters). Generally, bacteria are categorized, according to known pathogenicity within the uterus (Sheldon I. M., Noakes D. E., Rycroft A. N., Dobsons H. Effect of intrauterine administration of oestradiol on postpartum uterine bacterial infection in cattle. Animal Reproduction Science, 81:13-23 (2004)). The categories vary from 1 to 3 based in clinical endometritis, which correspond to:
Category 1—bacteria that frequently cause metritis;
Category 2—bacteria that are an infrequent cause of metritis; and
Category 3—bacteria not recognized as uterine pathogens.

Bacterial growth scores are summed-up for all bacteria (total bacterial score) or for each of the pathogen categories (1-3).

(ii) Biological status: by measuring artificial insemination performance, pregnancy hazard and milk yield (main parameters).

Example 6: In Vivo Effects of Casein Hydrolysate in Clinical Endometritis

The effect of bovine casein hydrolysate in comparison with control is evaluated in dairy cows suffering from clinical endometritis, in their postpartum period.

A routine examination of all cows in the herd within about 26 to 33 days postpartum includes a general physical examination and a clinical examination performed on the reproductive tract by transrectal palpation as well as rectal fever measurements, respiratory evaluation and heart beat measurements. Cows and heifers which are diagnosed with clinical endometritis based on clinical and bacteriology criteria which includes fever, typically high fever, bad smell, the presence of polymorphonuclear neutrophil granulocytes and microorganism/bacteria in endometrial (Sheldon et al., ibid 2006), but without previously being diagnosed with puerperal metritis, are recruited to the study.

The studied cows and/or heifer are assigned into two study groups a bovine casein hydrolysate (administered by intra uterine infusion) (Group I), and control (Group II).

Seven days post treatment (between about 33 and 40 days postpartum), each cow is clinically, cytology and bacteriology examined as in the enrollment. Animals which are still diagnosed with clinical endometritis and therefore are not clinically cured, receive a second dose of the same treatment as initially administered. These animals are then examined for a third and final time after additional 14 days (between about 47 and 54 days post partum; 21 days after initial enrollment).

Efficacy may be considered in the case groups with a clinical cure rate higher than 60% or a statistically significant result. The effect on cure rate will be determined primarily by changes in the bacteriological test results—i.e.

the presence of no microorganism according to Sheldon et al criteria (Sheldon et al ibid 2004) after at least one bacteriological test during the 7 to 9 days after treatment and null discharge detectable in the vagina.

Clinical bacteriology cure may be classified based on the following culture results (Sheldon et al ibid 2004).
  (i) Treatment success=cultures positive at clinical endometritis diagnosis and cultures negative after 7 days post treatment from the same microorganism which frequently cause metritis,
  (ii) Treatment failure=cultures positive for the same organism at clinical endometritis which frequently cause metritis on diagnosis day and 7 days post treatment,
  (iii) Inconsistent result=culture positive at clinical endometritis on diagnosis day and 7 days post treatment but with different organisms which frequently cause metritis.

Example 7: In Vivo Effect of Casein Hydrolysate in Sub-Clinical Endometritis

The effects of bovine casein hydrolysate are evaluated in dairy cows suffering from sub-clinical endometritis (Sheldon et al., ibid 2006).

A routine examination of all cows in the herd within about 26 to 33 days postpartum includes a general physical examination and a clinical examination performed on the reproductive tract by transrectal palpation as well as rectal fever measurements, respiratory evaluation and heart beat measurements. Cows and heifers which are diagnosed with sub-clinical endometritis based on clinical and cytology criteria which includes the presence of >18% polymorphonuclear neutrophil granulocytes in uterine cytology samples collected about 26-33 days postpartum, are recruited to the study.

The studied cows and/or heifer are assigned into two study groups a bovine casein hydrolysate (administered by intra uterine infusion) (Group I), and control (Group II). After 14 days post treatment (between about 40 and 47 days postpartum) each cow, case and controls, is clinically and cytology examined as in the enrollment. Animals still diagnosed with sub-clinical endometritis and therefore not clinically cured receive a second dose of bovine casein hydrolysate as initially administered or as specified by a veterinarian.

Efficacy may be considered in the case groups with a clinical cure rate higher than 60% or a statistically significant result, and/or measurement of less than 15% of polymorphonuclear neutrophil granulocytes or a statistically significant difference between cases and controls at the endometrial cytology examination, and/or biological status by measurement artificial insemination performance and/or pregnancy hazard. Clinical and cytology cure rate will be determined primarily by the cytology parameters.

Example 8: In Vivo Effect of Casein Hydrolysate in Acute Puerperal Metritis

The effects of bovine casein hydrolysate in comparison with control will be studied in dairy cows suffering from acute puerperal metritis (Sheldon et al., ibid 2006).

Following a routine examination of all cattle through about 7 to 14 days after calving, cattle which will be diagnosed with confirmed puerperal metritis according to the following clinical criteria, are enrolled to this study:

1) cows must be febrile (i.e., morning rectal temperature more than 39.5° C.-103.10° Fahrenheit), and
  2) cows must have a flaccid, non-retractable uterus that is located in the abdomen, and a watery, fetid vulvar discharge.

On the diagnosis day the tested cows are assigned into two study groups. Each group is administered twice a week by an interval of 48 hours with the following treatments of either bovine casein hydrolysate (Group I), or cephapirin benzathine (Group II).

Efficacy is assessed by comparing the examination of the clinical symptoms, bacteriology results and rectal temperature after enrollment, at first day of treatment and in each one of the consecutive about 7 to 14 days post treatment. Cows are observed with rectal temperatures taken after the animal's observation.

Treatment success is assessed on study day 7 to 14 after treatment. An animal is classified as successfully treated treatment if it has a rectal temperature of less than 39.5° C., bacteriological negative and non fetid vulval discharge.

Example 9: Pharmacokinetics of Bovine Casein Hydrolysate

In Vivo Bacterial Activity, Transmigration and Phagocytes Activity

A preliminary measurement of dose-response on bacterial activity, transmigration and phagocytes activity is performed after intrauterine infusion of bovine casein hydrolysate to dairy cows with confirmed uterine infections (clinical, bacteriological examination of uterine swabs) compared to controls.

Dose-depended response is assessed in three study or case groups, each group consisting of three cows. Each group receives the following intrauterine dose of bovine casein hydrolysate about 24 days post partum: 0.5 mg/kg (Group I), 2.5 mg/kg (Group II) and 4.4 mg/kg (Group III). The control group (Group IIII) consists of cows receiving at the same time as the study groups a solution as described in the protocol by intrauterine administration.

Endometrial cytology samples for determination of endometrial polymorphonuclear neutrophil granulocytes and phagocytic activity are collected AT 0, and around 12 and 24 hours after dosing. Further follow-up determinations are performed from endometrial cytology samples at 2, 5 and 7 days.

Cells are harvested from uterine lumen and counted using fluorescence microscopy. For the assessment of cell viability, the total number of viable polymorphonuclear neutrophil granulocytes after co-culture with bacterial products are determined with a quantitative flow cytometric standard cell dilution assay applying propidium iodide for the assessment of cell viability according the method by Hendrick A et al. (Hendricks A., Leibold W., Kaever V., Schuberth H.-J. Prostaglandin E2 is variably induced by bacterial superantigens in bovine mononuclear cells and has a regulatory role for the T cell proliferative response. Immunobiology, 201: 493-505 (2000)). For cultured bacteria, the supernatants of for example, *Escherichia coli* and *Arcanobacterium pyogenes*, after centrifugation 15,000 g, 20 minutes, 4° C., is removed, sterile-filtered (0.5 µm), and stored in aliquots at −80° C. Sediment bacterial are washed twice in sterile phosphate-buffered saline (PBS) and are disrupted into fragments by a French Pressure Cells and Press. Complete killing of the bacteria is judged by cultivate in blood agar (24 hours, 37° C., 5% $CO_2$ in air). The concentration of supernatants and bacterial fragments are expressed in equivalents of colony forming units (CFU) present in the suspension before preparation. For example, *Escherichia coli* preparation containing 3 μg/ml of lipopolysaccharide (LPS) (equivalent to $2\times10^8$ CFU/ml). Lipopolysaccharide contained in *Arcanobacterium* pyogenes are below the detection limits (<0.001 μg/ml).

In Vitro Chemotaxis

Chemotaxis of polymorphonuclear neutrophil granulocytes is also studied (in triplicates) in an acrylic transmigration chamber using 3 mm pore polycarbonate filters. The lower well of each of the transmigration chambers is filled with about 30 mL of bovine casein hydrolysate at different peptide concentrations, and with 300 μL of the chemokine rhIL-8 at concentrations of 0, 10, 25, 50, 100, 150, 200 rhIL-8 ng/mL medium and subsequently each well is under layered with 115 mL undiluted isotonic Percoll (100%). At the end of the assay, residual non-migrated polymorphonuclear neutrophil granulocytes cells from each upper well are collected. Upon removal of the membrane, migrated cells are harvested from the lower well of each chamber and cells from lower well and upper wells are quantified by flow cytometry using a Standard Cell Dilution Assay (SCDA) which quantify any subset of phenotypically definable, viable cells in heterogeneous populations using a FACScan flow cytometer (Pechhold K., Pohl T., Kabelitz D. Rapid quantification of lymphocyte subsets in heterogeneous cell populations by flow cytometry. Cytometry, 16:152-159 (1994)).

For subsequent in vitro experiments with migrated polymorphonuclear neutrophil granulocytes (evaluation of functional and phenotypical properties) the harvested cells are washed once with phosphate buffer saline (100×g, 4° C., 8 min) and re-suspended in cell culture medium (rhIL-8 ng/ml medium and undiluted isotonic Percoll (100%)) at $2\times10^6$ cells/ml where polymorphonuclear neutrophil will have >95% purity, >95% viability).

In Vitro Phagocytic Activity

A commercially available nonviable *Streptococcus zooepidemicus* suspension is labeled with fluoresceinisothiocyanat for phagocytic activity. The polymorphonuclear neutrophil granulocytes with ingested fluoresceinisothiocyanat-labeled streptococci is distinguished from non-phagocytic polymorphonuclear neutrophil granulocytes by increased green fluorescence after flow cytometric acquisition and analysis.

Example 10: In Vitro Model of Generation of Reactive Oxygen Species

Polymorphonuclear neutrophil granulocytes obtained from uterine scraping are stimulated with phorbol myristate acetate (PMA, 300 nmoL/l). The PMA serves as a receptor-independent activator of proteinkinase C and, thus, as a stimulator of reactive oxygen species (ROS)-formation. Phosphate buffer saline (PBS) instead of PMA serves as negative control. After 15 min (37° C. 5% $CO_2$ in air) of PMA induced activation of the leukocytes, the cells are loaded with the nonfluorescent dye dihydrorhodamin 123 (DHR 123, 15 μg/mL) is added to each of the wells. Short agitation and a third incubation phase (37° C. 5% $CO_2$ in air) of 15 min, allow for oxidative transformation of DHR 123 depending on the amount of ROS generated, into the green fluorescent rhodamin 123 via oxidation catalyzed by cellular myeloperoxidase. Subsequently all samples are placed on ice and kept in the dark until analysis by flow cytometry (2000 PMN) by determinate of the relative (mean) fluorescence intensity (Emmendörffer A., Hecht M., Lohmann-Matthes M. L., Roesler J. A fast and easy method to determine the production of reactive oxygen intermediates by human and murine phagocytes using dihydrorhodamin 123. J. Immunol. Method 131:269-275 (1990)).

The invention claimed is:

1. A method for treatment of an uterine infection, the method comprising administration to a female mammalian in need of treatment of uterine infection, an amount of at least one casein peptide, the amount being effective to treat an uterine infection in the mammalian animal, wherein the uterine infection is selected from the group consisting of toxic puerperal metritis, clinical metritis, perimetritis, clinical endometritis, sub-clinical endometritis, pyometra and cervicitis, and wherein the at least one casein peptide comprises an amino acid sequence selected from the group consisting of SEQ ID NO: 2, SEQ ID NO: 3, SEQ ID NO: 4, SEQ ID NO: 5 and SEQ ID NO: 6.

2. The method of claim 1, wherein the at least one casein peptide comprises one or more peptide fragments of β-casein, αS1-casein, αS2-casein, κ-casein.

3. The method of claim 1, wherein the at least one casein peptide is a casein hydrolysate.

4. The method of claim 1, wherein at least one casein peptide comprises a phosphopeptide.

5. The method of claim 1, wherein the uterine infection is selected from the group consisting of toxic puerperal metritis, clinical metritis, clinical endometritis and sub-clinical endometritis.

6. The method of claim 1, wherein the uterine infection is a post-partum infection.

7. The method of claim 1, wherein the female mammalian animal is a lactating animal.

8. The method of claim 6, wherein the female mammalian animal is selected from the group consisting of nulliparous, primiparous or multiparous lactating animal.

9. The method of claim 1, wherein the female mammalian animal is a cow.

10. The method of claim 1, wherein the at least one casein peptide is for use in combination with a pharmaceutical carrier for parenteral administration or for topical administration.

11. The method of claim 9, wherein administration comprises intrauterine administration or vaginal administration.

12. The method of claim 10, wherein administration is by transcervical intrauterine.

13. The method of claim 9, wherein parenteral administration is by injection or infusion.

14. The method of claim 1, wherein the at least one casein peptide is administered at a time period between calving.

15. The method of claim 13, wherein the time period comprises up to 120 days following calving.

16. The method of claim 14, wherein the time period comprises up to 70 days following calving.

17. The method of claim 14, wherein the time period is from day up to 33 days following calving.

18. The method of claim 13, wherein the administration comprises a single dose administration.

19. The method of claim 13, wherein the administration comprises two or more administrations of the at least one casein peptide, the two or more administrations comprise a time interval of from 1 hour to 14 days.

20. The method of claim 18, wherein administration comprises from two to six administrations.

21. The method of claim 1, wherein the amount of said at least one casein peptide effective to treat said uterine infection is between 10 ng/ml to 500 mg/ml.

\* \* \* \* \*